(12) United States Patent
Rehe

(10) Patent No.: US 11,454,801 B2
(45) Date of Patent: Sep. 27, 2022

(54) OPTICAL ARRANGEMENT FOR AN ENDOSCOPE AND ENDOSCOPE HAVING SUCH AN OPTICAL ARRANGEMENT

(71) Applicant: Henke-Sass, Wolf GmbH, Tuttlingen (DE)

(72) Inventor: Oliver Rehe, Wurmlingen (DE)

(73) Assignee: Henke-Sass, Wolf GmbH, Tuttlingen (DE)

( * ) Notice: Subject to any disclaimer, the term of this patent is extended or adjusted under 35 U.S.C. 154(b) by 568 days.

(21) Appl. No.: 16/200,624

(22) Filed: Nov. 26, 2018

(65) Prior Publication Data

US 2019/0162946 A1 May 30, 2019

(30) Foreign Application Priority Data

Nov. 27, 2017 (DE) .......................... 102017127931.8

(51) Int. Cl.
| | | |
|---|---|---|
| *G02B 23/24* | (2006.01) | |
| *G02B 3/06* | (2006.01) | |
| *A61B 1/002* | (2006.01) | |
| *A61B 1/00* | (2006.01) | |
| *G02B 5/20* | (2006.01) | |
| *G02B 27/14* | (2006.01) | |

(52) U.S. Cl.
CPC .......... *G02B 23/2446* (2013.01); *A61B 1/002* (2013.01); *A61B 1/00096* (2013.01); *G02B 3/06* (2013.01); *G02B 5/208* (2013.01); *G02B 23/243* (2013.01); *G02B 27/141* (2013.01)

(58) Field of Classification Search
CPC .. G02B 23/2446; G02B 5/208; G02B 27/141; G02B 3/06; G02B 23/243; G02B 23/24423; G02B 5/005; G02B 5/281; G02B 5/003; G02B 27/0018; G02B 23/24; G02B 5/201; G02B 5/285; A61B 1/002; A61B 1/00096
USPC ........................................................ 359/434
See application file for complete search history.

(56) References Cited

U.S. PATENT DOCUMENTS

| | | | | |
|---|---|---|---|---|
| 5,237,446 A | * | 8/1993 | Takahashi | .......... G02B 27/1006 348/337 |
| 5,833,596 A | * | 11/1998 | Bonnell | ................... A61B 5/01 600/109 |

(Continued)

FOREIGN PATENT DOCUMENTS

| | | |
|---|---|---|
| CN | 2706874 Y | 6/2005 |
| CN | 102116920 A | 7/2011 |

(Continued)

*Primary Examiner* — Stephone B Allen
*Assistant Examiner* — Rahman Abdur
(74) *Attorney, Agent, or Firm* — Skaar Ulbrich Macari, P.A.

(57) ABSTRACT

An optics arrangement for an endoscope is provided. The optics arrangement images an object situated in front of its distal end to the proximal end of the optics arrangement along a principal beam path having an optical axis. The optics arrangement is designed both for light from the visible spectrum and for light from the near infrared. The optics arrangement includes an aperture stop with a reflection layer in the principal beam path. The reflection layer reflects light from the visible spectrum and transmits light from the near infrared. The reflection layer is inclined in relation to the optical axis.

20 Claims, 2 Drawing Sheets

(56) References Cited

U.S. PATENT DOCUMENTS

| | | |
|---|---|---|
| 9,119,552 B2 * | 9/2015 | Baumann ............ A61B 1/00096 |
| 2002/0021511 A1 | 2/2002 | Lee et al. |
| 2005/0078175 A1 | 4/2005 | Kaneko |
| 2010/0182681 A1 | 7/2010 | Luecke et al. |
| 2011/0205651 A1 * | 8/2011 | Yamano ................ H04N 5/332 |
| | | 359/894 |
| 2014/0034835 A1 | 2/2014 | Frey et al. |
| 2015/0309225 A1 | 10/2015 | Moore |
| 2016/0370580 A1 * | 12/2016 | Takada .................. G02B 5/005 |
| 2017/0176736 A1 * | 6/2017 | Yamamoto ......... G02B 23/2476 |
| 2017/0269462 A1 * | 9/2017 | Maeda ................ H04N 9/3111 |

FOREIGN PATENT DOCUMENTS

| | | |
|---|---|---|
| CN | 202589483 U | 12/2012 |
| CN | 102998764 A | 3/2013 |
| CN | 103765289 A | 4/2014 |
| CN | 103984095 A | 8/2014 |
| CN | 104880806 A | 9/2015 |
| CN | 205083432 U | 3/2016 |
| CN | 206339783 U | 7/2017 |
| CN | 107111009 A | 8/2017 |
| CN | 206523666 U | 9/2017 |
| DE | 102004028616 A1 | 2/2006 |
| DE | 102010016264 A1 | 10/2011 |
| JP | H0854515 A | 2/1996 |
| JP | H10-197800 | 7/1998 |
| JP | 2006235139 A | 9/2006 |

* cited by examiner

OPTICAL ARRANGEMENT FOR AN ENDOSCOPE AND ENDOSCOPE HAVING SUCH AN OPTICAL ARRANGEMENT

PRIORITY

This application claims the benefit of German Patent Application No. 10 2017 127 931.8, filed on 27 Nov. 2017, which is hereby incorporated herein by reference in its entirety.

FIELD

The present invention relates to an optics arrangement for an endoscope and an endoscope having such an optics arrangement.

BACKGROUND

In optics arrangements used to perform imaging both in the visible spectrum and in the near infrared, it is often desirable for a great depth-of-field to be provided for the imaging in the visible range. As a rule, a weak signal is present in the near infrared region since fluorescence diagnostics, for example, are operated in this wavelength range. Therefore, it is often desirable for the greatest possible transmission through the optics arrangement to be provided for light from the near infrared.

Where possible, these properties for light from the visible wavelength range and light from the near infrared should be provided in such a way that no other optical properties of imaging in the visible wavelength range and imaging in the near infrared are worsened.

SUMMARY

The disclosure includes an optics arrangement for an endoscope. The optics arrangement can image an object situated in front of its distal end to the proximal end of the optics arrangement along a principal beam path having an optical axis, wherein the optics arrangement is designed both for light from the visible spectrum and for light from the near infrared and said optics arrangement comprises an aperture stop with a reflection layer in the principal beam path, said reflection layer reflecting light from the visible spectrum and transmitting light from the near infrared. The reflection layer is inclined in relation to the optical axis. Thus, it has an angle not equal to 90° in relation to the optical axis.

The production of unwanted ghost images is effectively prevented. The ghost images occur when the light from the visible spectrum reflected at the aperture stop is reflected back onto itself. As a result of the inclined reflection layer, the reflected light from the visible spectrum is no longer reflected back on itself according to the invention, but instead reflected to the side. Consequently, it is possible to form beam traps at the corresponding lateral positions such that the reflected light cannot lead to ghost images.

The inclination of the reflection layer can be chosen in such a way that light rays from the visible spectrum which strike the reflection layer parallel to the optical axis are reflected in such a way that they no longer extend parallel to the optical axis. In particular, the reflected light rays do not cross the optical axis (as seen in a side view on the optics arrangement). The reflected light rays preferably extend in a direction to the radial outer side of the optics arrangement. The reflection layer can be convexly or concavely curved.

The reflection layer can be embodied in a ring-shaped region or can be embodied as a ring-shaped reflection layer. The ring-shaped region or the ring-shaped reflection layer can be intrinsically closed. However, it is also possible for one or more gaps to be present in the circumferential direction and/or in a direction transverse to the circumferential direction. Preferably, no part of the reflection layer is formed in the gap or gaps.

The aperture stop preferably comprises a first region with the reflection layer and a second region in which the reflection layer is not formed. Consequently, the first region can relay substantially only light from the near infrared (no light from the visible spectrum), for example, and the second region can relay both light from the visible spectrum and light from the near infrared, for example.

The aperture stop is preferably embodied as a transmissive stop (in relation to the light relayed through the aperture stop).

What the ring-shaped reflection layer or the embodiment of the reflection layer in a ring-shaped region achieves is that the aperture diameter for light from the visible spectrum is smaller than for light from the near infrared. Consequently, the desired great depth-of-field for images with light from the visible spectrum is ensured.

Moreover, the aperture diameter for light from the near infrared can be larger than for light from the visible spectrum, and so the desired greatest-possible transmission for light from the near infrared can be ensured.

Consequently, the aperture stop is a wavelength-dependent aperture stop, the aperture diameter of which for light from the near infrared can be greater than for light from the visible spectrum.

The reflection layer can be embodied on a curved side of a transparent body.

The curved side can be a spherically curved side. However, an aspherical curvature is also possible. However, any other curvature profile that prevents the reflected light from the visible spectrum being reflected back onto itself is also possible.

The aperture stop can comprise two interconnected transparent bodies, the sides of which facing one another having a complementary curvature profile and the sides of which pointing away from one another having a plane embodiment, the reflection layer being arranged between the sides of the two bodies facing one another.

The two transparent bodies can be formed from the same material (e.g., glass or plastic) or from different materials (e.g., different glasses, different plastics, plastic and glass). In particular, the two bodies can be embodied as a plano-convex lens and plano-concave lens.

The connection between the two bodies can be realized by cementing or contact bonding, for example.

The transparent body positioned closer to the distal end can comprise a peripheral area, which is blackened. Hence, the peripheral area of this body can already serve as a beam trap for the reflected light from the visible spectrum.

The optics arrangement can comprise a beam trap for the light from the visible spectrum that is reflected by the ring-shaped reflection layer. By way of example, this beam trap can be embodied in a mount of the aperture stop.

The ring-shaped reflection layer can have an annular embodiment. However, any other ring shape is also possible. In particular, the inner contour of the ring-shaped reflection layer can be circular, ellipsoid, oval, star-shaped or polygonal.

The reflection layer can be embodied as a dielectric layer or as a dielectric layer system. Hence, it is easily possible to very exactly set the wavelength range that is reflected and set the wavelength range that is transmitted. Moreover, such a dielectric layer or such a dielectric layer system can have a very thin embodiment, which is further advantageous in relation to the avoidance of unwanted aberrations for light from the visible spectrum and/or light from the near infrared.

The aperture stop can be embodied in such a way that it has no optical refractive power. Thus, the aperture stop can have the optical effect of a plane-parallel plate, for example.

The aperture stop can be arranged in a portion of the principal beam path in which a collimated beam profile is present.

The optical arrangement can comprise an objective lens at the distal end and a relay system following the objective lens. The aperture stop can be arranged in the relay system. In particular, the aperture stop can be positioned in the relay system as a separate component. Moreover, it is possible to integrate the aperture stop in a two-part or a multi-part rod lens, for example. Thus, the reflection layer can be embodied on a curved surface of a rod lens or of an element of a rod lens (which is preferably connected to a surface of a further element of the rod lens with a complementary curvature), for example.

The disclosure also includes an endoscope. The endoscope can comprise a main part, an endoscope shaft connected to the main part and an optics arrangement as disclosed herein (including the developments thereof), wherein the optics arrangement is preferably at least partly arranged within the endoscope shaft.

The endoscope can be embodied as a medical or technical endoscope. Further, the endoscope according to the invention can be hermetically sealed and/or autoclavable.

The endoscope shaft can be embodied as a rigid endoscope shaft, as an endoscope shaft with a bendable distal end or as a flexible endoscope shaft.

At the end of the main part facing away from the endoscope shaft, the endoscope may comprise a camera connector, to which a camera can be attached (e.g., in a detachable fashion), it being possible to record the object imaged by means of the optics arrangement using said camera. The camera can be embodied in such a way that it can record both an image using light from the visible spectrum and an image using light from the near infrared (simultaneously and/or sequentially in time).

The disclosure includes a system comprising an endoscope as disclosed herein and a camera connected therewith.

It is understood that the features specified above and the features yet to be explained below can be used not only in the specified combinations but also in other combinations or on their own, without departing from the scope of the present invention.

Figure 1:
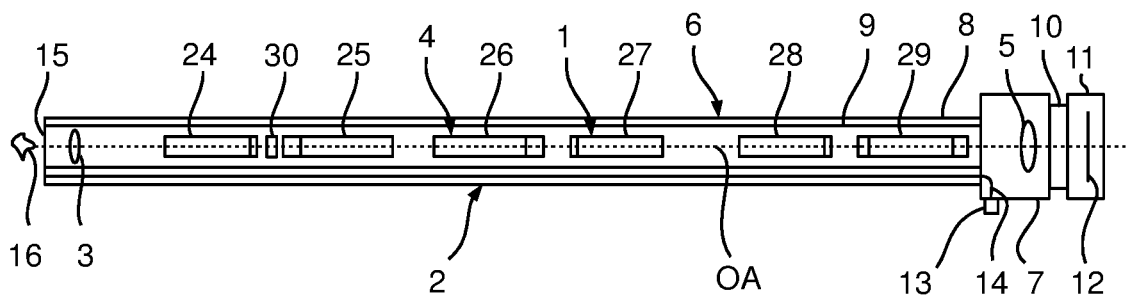
FIG. 1 is a schematic illustration of the optics arrangement according to certain embodiments in an endoscope.

While the invention is amenable to various modifications and alternative forms, specifics thereof have been shown by way of example in the drawings and will be described in detail. It should be understood, however, that the intention is not to limit the invention to the particular example embodiments described. On the contrary, the invention is to cover all modifications, equivalents, and alternatives falling within the scope of the invention as defined by the appended claims.

DETAILED DESCRIPTION

The invention is explained in yet more detail below with the aid of embodiment examples with reference to the attached drawings, which also disclose features essential to the invention. These embodiment examples merely serve the purpose of illustration and are not to be interpreted as limiting. For example, a description of an embodiment example with a plurality of elements or components is not to be interpreted to the effect that all of these elements or components are necessary for the implementation. Rather, other embodiment examples can also contain alternative elements and components, fewer elements or components or additional elements or components.

Elements or components of different embodiment examples can be combined with each other, unless otherwise indicated. Modifications and alterations which are described for one of the embodiment examples can also be applicable to other embodiment examples. To avoid repetitions, the same or corresponding elements are given the same reference numbers in different figures and are not explained repeatedly.

Light from the visible spectrum is understood to mean light with a wavelength from the range from 380 to 750 nm and, in particular, from 400 to 700 nm. Light from the near infrared is understood to mean light with a wavelength from the range from 780 nm to 3 µm and, in particular, from 780 nm to 1500 nm. In any case, there is no overlap between the wavelength ranges for light from the visible spectrum and light from the near infrared.

In the embodiment shown in FIG. 1, the optics arrangement 1 according to the invention is shown in a schematically illustrated endoscope 2. At its distal end, the optics arrangement 1 comprises an objective lens 3, which is followed by relay optics 4 and an eyepiece 5.

The endoscope 2 comprises a shaft 6 and a main part 7 connected therewith. The shaft 6 comprises an outer tube 8, in which an optics tube 9 with a smaller cross section is located. As illustrated in FIG. 1, the objective lens 3 and the relay optics 4 are arranged in the optics tube 9. The eyepiece 5 is positioned in the main part 7.

A camera connector 10, to which a camera 11 is detachably fastened, may be provided at the end of the main part 7 pointing away from the shaft 6. The camera 11 may comprise optics (not shown) and a planar image sensor 12. By way of example, the image sensor 12 can be a CCD sensor or a CMOS sensor. The camera 11 can be not only connected directly to the camera connector 10, as shown in FIG. 1. It is also possible for a coupler (not shown) to be interposed between the camera connector 10 and the camera 11, said coupler in turn possibly containing optics. Furthermore, it is possible for an eye lens (not shown) to be provided instead of the camera connector 10.

An illumination connector 13 is formed on the main part 7, said illumination connector being connected to optical fibres 14 (only a single one of which is plotted in FIG. 1 in a representative manner) which extend from the illumination connector 13 to the distal end 15 of the shaft 6 through a region between the outer tube 8 of the shaft 6 and the optics tube 9 and which emit the light there for the purposes of illuminating an object 16.

The optics arrangement 1 is embodied in such a way that the object 16 is imaged on the image sensor 12, the optics arrangement 1 being designed to be suitable for both light from the visible spectrum and for light from the near infrared. By way of example, this is understood to mean that both the imaging with light from the visible spectrum and the imaging with light from the near infrared is implemented in focus on the image sensor 12 (or into the same plane or focal plane). In particular, light from the visible spectrum is understood to mean light with a wavelength from the range from 380 to 750 nm and, in particular, from 400 to 700 nm. Here, in particular, light from the near infrared is understood to mean light with a wavelength from the range from 780 nm to 3 μm and, in particular, from 780 nm to 1500 nm.

Figure 2:
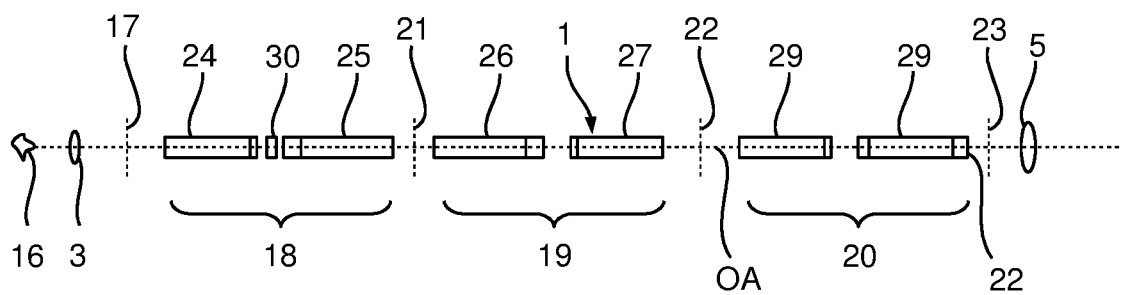
FIG. 2 is a schematic illustration of the optics arrangement of FIG. 1.

The objective lens 4, which is arranged at the distal end of the optics arrangement, images the object 16 into a first intermediate image plane 17, which may also be referred to as a distal intermediate image plane 17 (FIG. 2). The relay optics 4 is embodied as a rod lens system having a first, a second and a third inverting stage 18, 19, 20, which are arranged in succession and which each image an intermediate image into a next intermediate image plane. Thus, the first inverting stage 18 images the intermediate image lying in the first intermediate image plane 17 into a second intermediate image plane 21. The second inverting system 19 images the intermediate image lying in the second intermediate image plane 21 into a third intermediate image plane 22. The third inverting system 20 images the intermediate image from the third intermediate image plane 22 into a fourth intermediate image plane 23, which may also be referred to as proximal intermediate image plane 23. Consequently, the three inverting systems 18-20 are arranged in succession in such a way that an intermediate image lying in the distal intermediate image plane 17 is imaged into the proximal intermediate image plane 23 (via the respective next intermediate image plane 21 and 22). Since each inverting stage 18-20 produces an inverted intermediate image when imaging the intermediate image and since an odd number of inverting stages 18-20 is provided, the intermediate image of the object 16 lying in the distal intermediate image plane 17 is imaged as an inverted intermediate image into the proximal intermediate image plane 23. Therefore, the relay optics 4 can also be referred to as an inverting system 4. The intermediate image produced in the proximal intermediate image plane 23 is imaged on the image sensor 12 by means of the eyepiece 5. Here, each inverting stage 18-20 comprises two rod lenses 24, 25 and 26, 27 and 28, 29, respectively, which may have the same embodiment or different embodiments.

The region from the objective lens 3 to the eyepiece 5 can be referred to as a principal beam path with an optical axis OA, along which the light rays from the visible spectrum and the light rays from the near infrared extend for the purposes of the above-described imaging.

Figure 3:
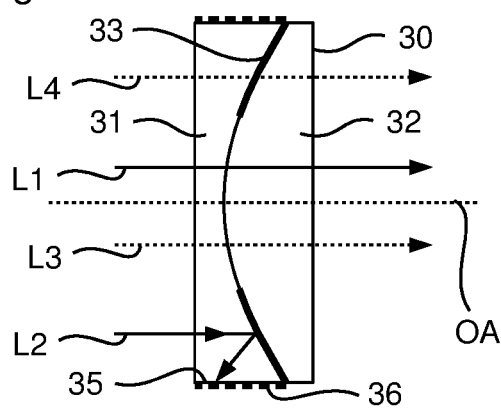
FIG. 3 is a magnified view of the aperture stop from the optics arrangement according of FIGS. 1 and 2.
Figure 4:
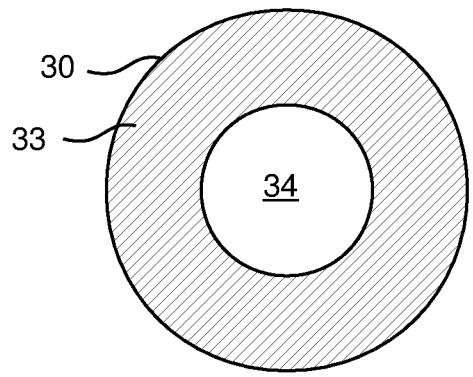
FIG. 4 is a plan view of the aperture stop of FIG. 3.

An aperture stop 30, which is illustrated in magnified fashion in FIG. 3, is arranged between the rod lenses 24 and 25 of the first inverting stage 18. FIG. 4 shows a plan view of the aperture stop 30 according to FIG. 3.

The aperture stop 30 comprises a plano-concave lens 31 and a plano-convex lens 32, the interconnected curved sides of which facing one another having complementary curvatures. The curvatures are spherical in each case. A ring-shaped reflection layer 33 (which has convex curvature here) is formed between the two interconnected curved sides, said reflection layer reflecting light from the visible spectrum and transmitting light from the near infrared. The reflection layer 33 is illustrated using hatching in FIG. 4.

The sides of the plano-concave lens 31 and of the plano-convex lens 32 pointing away from one another have a planar embodiment in each case. Since the two lenses 31 and 32 are formed from the same material, the aperture stop 30, from an optical point of view, is a plane-parallel plate, which is positioned in a region of the collimated beam profile in the relay optics 4 and therefore, from an optical point of view, has no imaging effect. Furthermore, the optical path length for light from the visible spectrum that passes through the aperture stop 30 is always the same, independently of the position relative to the optical axis OA. The same applies to light from the near infrared.

The reflection layer 33, which may be embodied as a dielectric layer or as a dielectric layer system, is designed in such a way that it reflects light from the visible spectrum (as completely as possible). This leads to light from the visible spectrum being transmitted in a central region 34 of the aperture stop 30, as indicated schematically by the light ray L1. Light from the visible spectrum that strikes the aperture stop 30 outside of the central region 34 is reflected back by the reflection layer 33. However, since the reflection layer 33 has an embodiment that is inclined in relation to the optical axis OA (i.e., has an angle of not equal to 90°), the light is not reflected back onto itself but reflected to the side. This is plotted schematically for the light ray L2, which strikes the peripheral area 35 of the plano-convex lens 31. In the embodiment described here, the peripheral area 35 has a blackened embodiment and serves as beam trap 36 for the light rays L2 reflected by the reflection layer 33.

The reflection layer 33 transmits light from the near infrared, and so it is not only light striking the central region 34 that is transmitted but also light striking the reflection layer 33. This is indicated in FIG. 3 by the light rays L3 and L4. Hence, the aperture diameter for light from the near infrared is greater than the aperture diameter for light from the visible spectrum. Consequently, the aperture stop 30 is a wavelength-dependent aperture stop, which firstly ensures the desired great depth-of-field for imaging with light from the visible spectrum (on account of the small aperture diameter). Here, the production of ghost images, which arise when the light from the visible spectrum is reflected back onto itself, is reliably prevented. Secondly, the aperture stop 30 has a larger diameter for light from the near infrared, which is advantageous since the signal or the available amount of light in this wavelength range is frequently relatively low.

Firstly, being able to ensure a good optical imaging quality in the case of light from the visible spectrum (great depth-of-field and the prevention of ghost images) and a good signal-to-noise ratio for light from the near infrared is consequently advantageously achieved by means of the aperture stop 30 according to the invention.

Figure 5:
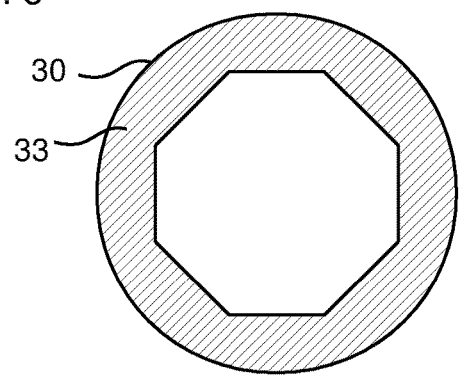
FIGS. 5-10 each show a plan view of the aperture stop according to further exemplary embodiments.
Figure 6:
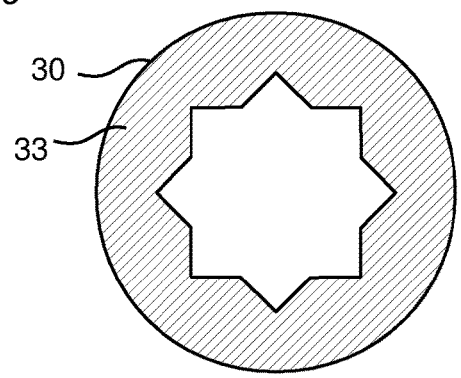

As shown in FIGS. 3 and 4, the ring-shaped reflection layer 33 is embodied as an annulus. However, any other ring shape may also be present. In particular, the inner contour of the ring-shaped reflection layer 33 may have a polygonal form, for example, as shown in FIG. 5. Here, the polygonal form corresponds to a regular octagon. FIG. 6 illustrates a star-shaped internal contour as an example.

The reflection layer 33 can be evaporated onto the convex side of the plano-convex lens 32 or onto the concave side of the plano-concave lens 31. As a result of this type of embodiment of the reflection layer, the thickness of the reflection layer, and hence the edge for delimiting the central region 34, is very thin, and so bothersome aberrations for the light from the visible wavelength range and/or for the light from the near infrared hardly occur at this edge.

The blackening 36 of the peripheral area 35 is only one example of a beam trap for the reflected light from the visible spectrum. Any other type of beam trap may also be used. By way of example, the corresponding mounting region of the mount (not plotted) may thus be blackened. It is also possible for terraced black beam traps to be formed.

The curved sides of the two lenses 31 and 32 preferably have spherical curvature. However, an aspherical curvature is also possible. Further it is possible, for example, to use appropriate axicons instead of the lenses 31, 32. It is essential that the two lenses 31, 32 or transparent bodies comprise sides facing one another with a complementary embodiment, said embodiments deviating from the planar form. The connection between the two lenses 31, 32 or between the two bodies 31, 32 can be realized by cementing or contact bonding, for example.

A glass material is preferably used as a material.

In the embodiment described here, the central region 34 can have a diameter in the range from 1 to 7 mm. The outer diameter of the reflection layer 33 can lie in the range from 2.5 to 12 mm. The thickness of the aperture stop 30 along the optical axis OA can lie in the range from 1.5 to 2.5 mm.

The arrangement of the aperture stop 30 in the first inverting stage 18 is preferable. However, the aperture stop 30 can also be positioned at other points in the optics arrangement. Preferably, it is positioned at a point with a collimated beam profile. Further, it is possible to directly integrate the aperture stop 30 into one of the rod lenses 24-29. Thus, for example, the rod lens 24 can have a two-part embodiment, wherein the interconnected sides facing one another have complementary curvatures and the reflection layer 33 is embodied on one of these sides.

Figure 7:
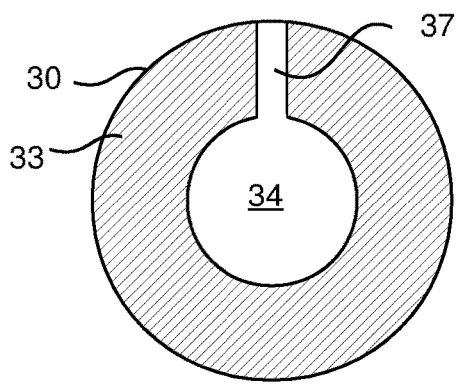

In the previously described exemplary embodiments, the ring-shaped reflection layer 33 is always intrinsically closed. However, it is also possible for the reflection layer 33 to have a gap 37 extending transversely to the circumferential direction, for example, the reflection layer 33 not being formed in said gap, as illustrated in FIG. 7. Naturally, it is also possible to provide a plurality of gaps 37 extending transversely to the circumferential direction (not shown).

Figure 8:
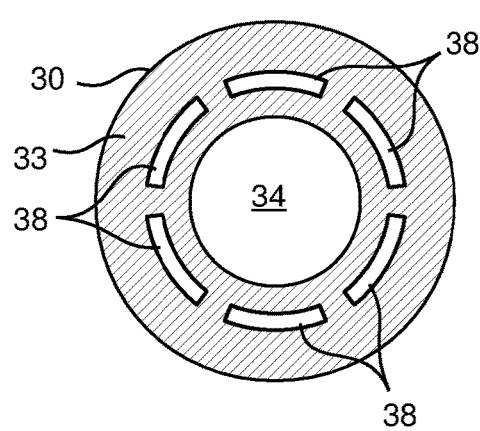
Figure 9:
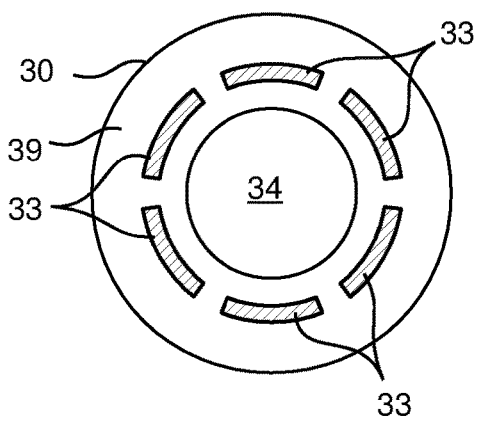
Figure 10:
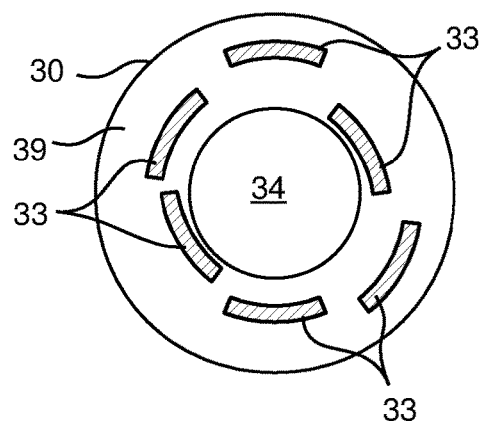

Further, it is possible for the reflection layer 33 to have one or, as shown in FIG. 8, more gaps 38 extending in the circumferential direction. In the exemplary embodiment shown in FIG. 8, the gaps 38 have a regular arrangement. An irregular arrangement may also be present. Additionally, the individual gaps 38 can differ in terms of their dimensions. In the exemplary embodiment shown in FIG. 9, the aperture stop 30 comprises a ring-shaped region 39, which surrounds the central region 34. The reflection layer 33 is arranged in the ring-shaped region 39. In the exemplary embodiment shown in FIG. 9, the reflection layer 33 comprises a plurality of portions which can be ring-shaped portions, for example. However, the form and dimensions of the individual portions of the reflection layer 33 can also be different and can have different forms. Nor is the regular arrangement according to FIG. 9 necessary. As shown in FIG. 10, an irregular arrangement of the portions 33 is possible.

While the invention has been described in connection with what is presently considered to be the most practical and preferred embodiments, it will be apparent to those of ordinary skill in the art that the invention is not to be limited to the disclosed embodiments. It will be readily apparent to those of ordinary skill in the art that many modifications and equivalent arrangements can be made thereof without departing from the spirit and scope of the present disclosure, such scope to be accorded the broadest interpretation of the appended claims so as to encompass all equivalent structures and products. Moreover, features or aspects of various example embodiments may be mixed and matched (even if such combination is not explicitly described herein) without departing from the scope of the invention.

What is claimed is:

1. An optics arrangement for an endoscope, wherein the optics arrangement images an object situated in front of a distal end of the optics arrangement to a proximal end of the optics arrangement along a principal beam path, the principal beam path having an optical axis, wherein the optics arrangement is configured both for a visible spectrum of light and a near infrared spectrum of light, the optics arrangement comprising:
an aperture stop with a reflection layer in the principal beam path, said reflection layer reflecting light from the visible spectrum of light and transmitting light from the near infrared spectrum of light,
wherein the reflection layer is inclined in relation to the optical axis,
wherein the aperture stop comprises two transparent bodies that are interconnected such that the two transparent bodies do not move relative to one another, and
wherein each of the two transparent bodies include a respective side that faces the other and an opposing side facing away from the other.

2. The optics arrangement of claim 1, wherein the reflection layer is defined in a ring-shaped region.

3. The optics arrangement of claim 1, in which the reflection layer is ring-shaped.

4. The optics arrangement of claim 3, wherein the ring-shaped reflection layer is annular.

5. The optics arrangement of claim 1, wherein the reflection layer is formed on a curved side of a transparent body.

6. The optics arrangement of claim 5, wherein the curved side has a spherical curvature.

7. The optics arrangement of claim 1, wherein each of the respective sides that face each other are curved such as to have a complementary curvature profile with the other, and wherein each of the opposing sides comprises a planar surface.

8. The optics arrangement of claim 7, wherein a transparent body positioned closest to the distal end comprises a peripheral area, and wherein the peripheral area is blackened.

9. The optics arrangement of claim 7, wherein the two transparent bodies are formed from the same material.

10. The optics arrangement of claim 7, wherein the two transparent bodies form a rod lens or are part of a rod lens.

11. The optics arrangement of claim 1, further comprising a beam trap provided to the optics arrangement such that light from the visible spectrum is reflected by the reflection layer.

12. The optics arrangement of claim 1, wherein the reflection layer comprises a dielectric layer or a dielectric layer system.

13. The optics arrangement of claim 1, wherein the aperture lens is arranged in a portion of the principal beam path with a collimated beam profile.

14. The optics arrangement of claim 1, wherein the aperture stop has no optical refractive power.

15. The optics arrangement of claim 1, further comprising an objective lens disposed at the distal end and a relay system follows the objective lens, wherein the aperture stop is arranged in the relay system.

16. An endoscope, comprising:
a main part,
an endoscope shaft connected to the main part; and an optics arrangement according to claim 1,
wherein the optics arrangement is at least partly disposed within the endoscope shaft.

17. The optics arrangement of claim 1, wherein the reflection layer is arranged between the respective sides that face one another.

18. An optics arrangement for an endoscope, wherein the optics arrangement images an object situated in front of a distal end of the optics arrangement to a proximal end of the optics arrangement along a principal beam path, the principal beam path having an optical axis, wherein the optics arrangement is configured both for a visible spectrum of light and a near infrared spectrum of light, the optics arrangement comprising:
 an aperture stop with a reflection layer in the principal beam path, said reflection layer reflecting light from the visible spectrum of light and transmitting light from the near infrared spectrum of light,
 wherein the reflection layer is inclined in relation to the optical axis,
 wherein the aperture stop comprises two transparent bodies that each have a respective side that faces the other one of the two transparent bodies,
 wherein the reflection layer is disposed between the respective sides that face one another such that the reflection layer contacts each of the respective sides that faces the other.

19. The optics arrangement of claim 18, wherein the two transparent bodies are interconnected such that the two transparent bodies do not move relative to one another.

20. The optics arrangement of claim 18, wherein each of the respective sides that face each other are curved such as to have a complementary curvature profile with the other.

* * * * *